United States Patent [19]

Dynes et al.

[11] Patent Number: 5,191,097
[45] Date of Patent: Mar. 2, 1993

[54] PRODUCTION OF FATTY ACID SALTS

[75] Inventors: James W. Dynes; Gerard J. Gutowski, both of Tiffin, Ohio; M. Stephen Lajoie, Basking Ridge, N.J.

[73] Assignee: Church & Dwight Co., Inc., Princeton, N.J.

[21] Appl. No.: 761,234

[22] Filed: Sep. 17, 1991

[51] Int. Cl.$^5$ .............................................. G07C 51/00
[52] U.S. Cl. .................................................... 554/156
[58] Field of Search ......................... 260/413; 554/156

[56] References Cited

U.S. PATENT DOCUMENTS 4,826,694  8/1989  McAskie .............................. 426/74

OTHER PUBLICATIONS

Chemical Abstract, vol. 95, #9, p. 607, 1981, 78791q.

Primary Examiner—Jose G. Dees
Assistant Examiner—Deborah D. Carr
Attorney, Agent, or Firm—Charles B. Barris

[57] ABSTRACT

In one embodiment this invention provides an improved process for the production of fatty acid calcium salt. An important feature of the process is the utilization of a residual effluent byproduct stream from a sodium bicarbonate manufacturing plant as the aqueous medium of the fatty acid calcium salt-forming reaction process.

4 Claims, No Drawings

PRODUCTION OF FATTY ACID SALTS

BACKGROUND OF THE INVENTION

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Fat is an excellent energy source, and it is known that if the proportion of fat in cattle food is increased, lactating dairy cattle produce high milk yields without draining their reserves of body fat and without diminishing the proportion of milk fat in the milk produced.

However, it has been found that if the proportion of fat in the diet of cattle exceeds about 2% of the total feed solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats. Although the decreased fiber digestion in the rumen is partially compensated by greater fiber digestion in the lower parts of the alimentary canal, such later fiber digestion produces a blend of different fatty acids than that which is produced by the digestion in the rumen, and the different blend of fatty acids is less suited to the cow's metabolism.

There has been a continuing need for new dietary supplements for animal feed which can be fed to ruminant animals without interfering with the rumen microorganisms.

U.S. Pat. Nos. 4,642,317; 4,826,694; 4,853,233; and 4,909,138 describe the incorporation of insoluble fatty acid salts in ruminant feed as a means of increasing the fat content of the feed without deleteriously affecting the ruminant digestion cycle. A feed additive such as fatty acid calcium salt functions as a rumen bypass product, and is subsequently metabolized in the abomasum or small intestine of the ruminant.

Also of background interest with respect to the present invention are the important environmental ramifications of the generation and accumulation and disposal of residual effluent streams from chemical manufacturing industries. Stringent waste disposal regulations have spurred the search for ecologically acceptable means of chemical byproduct disposal or utilization.

Accordingly, it is an object of the invention to provide a fatty acid salt composition which can function as a rumen bypass animal feed supplement, and permit a beneficial increase in the dietary fat content of the feed.

It is another object of this invention to provide a novel process for production of a fatty acid salt, in which a residual byproduct effluent from a chemical manufacturing operation is incorporated as a reactive aqueous medium.

Other objects and advantages of the present invention shall become apparent from the accompanying description and examples.

DESCRIPTION OF THE INVENTION

One or more objects of the present invention are accomplished by the provision of a process for the preparation of a fatty acid salt product which comprises (1) forming an admixture of reactive ingredients comprising (a) at least one $C_{14}$-$C_{22}$ fatty acid, (b) calcium oxide in at least an equivalent weight quantity for salt formation with the fatty acid, and (c) between about 10-50 weight percent, based on the weight of fatty acid, of an aqueous solution of sodium carbonate-bicarbonate, wherein the aqueous solution is a residual effluent from a sodium bicarbonate-producing process, and the solution contains between about 0.2-5 weight percent of sodium in the form of sodium carbonate-bicarbonate; and (2) recovering the salt product after completion of the exothermic salt-forming reaction.

The $C_{14}$-$C_{22}$ fatty acid component of the salt-forming reaction medium consists of one or more saturated or unsaturated carboxylic acids such as those derived from beef and mutton tallow, lard, cottonseed oil, palm oil, and the like.

Palm fatty acid distillate is a commercial product produced by distilling the fatty acids present in natural palm oil. A distillate product typically has the following weight percent content:

| | |
|---|---|
| Free fatty acids | 60–90 |
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram. The fatty acids in the free fatty acids and the triglycerides consist of the following weight percent:

| | |
|---|---|
| Palmitic acid | 38–50 |
| Oleic acid | 35–40 |
| Linoleic acid | 5–10 |
| Stearic acid | 3–6 |
| Lauric acid | 1–3 |

Beef tallow acids are available commercially as a byproduct obtained by alkaline extraction of waste beef fat and subsequent acidification, and normally contain the following weight percent of fatty constituents:

| | |
|---|---|
| Free fatty acids | 60–90 |
| Triglycerides | 10–40 |
| Water | <1 |
| Unsaponifiables | <3 |

The iodine value is less than 50 and the melting point is 40°–45° C. The content of peroxides is less than 10 milliequivalents of oxygen per kilogram. The fatty acids in the free fatty acids and in the triglycerides have the following weight percent content:

| | |
|---|---|
| Palmitic acid | 22–28 |
| Oleic acid | 38–44 |
| Linoleic acid | 3–6 |
| Stearic acid | 18–24 |

Because $C_{14}$-$C_{22}$ fatty acids and glycerides are susceptible to atmospheric oxidation, it is advantageous to incorporate an oil-soluble antioxidant, and a chelating agent to bind any ferric, copper, zinc or other metal capable of catalyzing atmospheric oxidation. Suitable quantities for inclusion in the fatty acid bulk are about 0.03–0.08% of antioxidant, and about 0.05–0.3% of chelating agent, based on the weight of fatty acid.

Illustrative of preferred additives are butylated hydroxytoluene antioxidant and citric acid chelating agent. The chelating agent is added in an edible solvent such as propylene glycol to facilitate blending into the fatty acid.

The calcium oxide component of the process can be utilized either alone or in combination with magnesium oxide. The calcium oxide component can be calcined limestone, which contains 93-96% CaO and not more than about 7% of $CaCO_3$. The basic oxide preferably has a particle size which passes a 150μ mesh screen.

As noted previously, the aqueous phase of the salt-forming reaction system is provided in the form of an aqueous solution of sodium carbonate-bicarbonate. The aqueous solution is a residual effluent from a sodium bicarbonate-producing process, and contains between about 0.2-5 weight percent of sodium in the form of a sodium carbonate-bicarbonate mixture.

The residual effluent typically is derived from a plant scale manufacturing operation in which sodium carbonate is carbonated to sodium bicarbonate. The residual effluent stream generated from the carbonation process typically has a sodium ion content of about 0.2-2 weight percent. A higher sodium content can be obtained if desired by evaporating a portion of the aqueous medium, or by utilizing a more concentrated solution such as a purge stream from the main reactor.

The invention process can be conducted in a batch reactor or as a continuous operation. The fatty acid, calcium oxide and aqueous medium can be admixed simultaneously, or the fatty acid and calcium oxide can be blended first and then combined with the aqueous medium.

In one method the fatty acid is heated to 80°-110° C. or higher, and then mixed with the basic oxide. After the aqueous medium is added to the mixture, there is a short induction period which is followed by an exothermic salt-forming reaction.

The amount of aqueous medium employed is sufficient to support the salt-forming reaction, and preferably is vaporized as steam during the exothermic reaction period to yield a friable fatty acid salt product which in granule form is suitable for use as an animal feed supplement.

An important advantage of the present invention process is the value-added utilization of a residual effluent from a chemical manufacturing plant, which has both environmental and economic consequences.

Another advantage of the invention process is in the efficiency of insoluble fatty acid calcium salt formation. It appears that the sodium carbonate-bicarbonate salt present in the aqueous medium component reacts readily with the fatty acid component to form an intermediate fatty acid sodium salt. Subsequently the fatty acid sodium salt interacts with the hydrated calcium oxide to produce the insoluble fatty acid calcium salt product. If the sodium content in the original aqueous effluent stream is at least about 1.0 weight percent, the kinetically favorable sodium salt intermediate reaction converts essentially all of the fatty acid from free acid to a sodium salt intermediate. Without the presence of the basic sodium ions, the kinetically less favorable reaction of calcium ions with fatty acid tends to be incomplete and some residual unreacted fatty acid remains under the processing conditions. The presence of sodium ions facilitates the conversion of fatty acid via the sodium salt intermediate to its calcium salt derivative.

The following Examples are further illustrative of the present invention. The components and specific ingredients are presented as being typical, and various modifications can be derived in view of the foregoing disclosure within the scope of the invention.

The present patent application subject matter is related to that disclosed in copending patent application Ser. No. 761,235, filed Sep. 17, 1991, now pending. The related patent application describes a process for producing metal salts of fatty acids, utilizing a mixture of alkali metal and alkaline earth metal compounds as a basic salt-forming reactant.

EXAMPLE I

This Example illustrates the continuous production of fatty acid calcium salt in accordance with the present invention.

The fatty acid component is a palm fatty acid distillate of the following composition:

| | |
|---|---|
| Lauric acid | 2.3% |
| Palmitic acid | 49.9% |
| Stearic acid | 5.4% |
| Oleic acid | 35.0% |
| Linoleic acid | 7.4% |

The residual effluent aqueous medium is obtained from a Church & Dwight Co., Inc. sodium bicarbonate manufacturing plant in Old Fort, Ohio. The aqueous medium contains about 4.2% sodium carbonate-bicarbonate.

The process is operated continuously with equipment which is essentially the same as described and illustrated with reference to FIG. 1 of U.S. Pat. No. 4,826,694 by W. McAskie.

Calcium oxide from a hopper and hot palm oil distillate (96° C.) from a supply line are mixed in predetermined proportions in a mixing pump. The residual effluent aqueous medium is added to the reactant blend by a supply line.

The hydrated mixture is passed through a mixing pump and the resultant semi-liquid reaction medium at about 100° C. is discharged as a spread layer onto a continuously moving conveyor belt. Steam and carbon dioxide evolve from the conveyor transported reaction mass.

At the end of the conveyor belt solid lumps of reaction product fall through a sizing machine onto a second conveyor belt. In this conveying zone the salt-forming reaction and evolution of water proceed to completion. The essentially dry fatty acid calcium salt product is passed through a sifter, and collected in bags suitable for transportation and storage.

The residence time on the first conveyor is about 30 minutes, and the overall production time from reactant mixing to collection of the dry granulated product is about 2.25 hours.

The final product has a total fatty acid calcium salt content of 85 weight percent, a water content of about 3-5 weight percent, and an ash content of about 15 weight percent.

The invention fatty acid calcium salt product can be incorporated as a dietary supplement in cattle feed such as hay silage or corn silage, in a calculated quantity which will provide each animal about 100 grams per day of fatty acid salt.

EXAMPLE II

This Example illustrates the effect of sodium carbonate or sodium bicarbonate concentration on the salt-forming process for production of fatty acid calcium salt.

A series of batch reactions are conducted for the preparation of palm oil distillate calcium salt. The palm oil distillate is the same as described in Example I.

In each preparation, aqueous sodium carbonate or sodium bicarbonate solution (30.6 g) is admixed with calcium oxide (24.7 g) and palm oil distillate (167.6 g).

The Table summarizes the reaction temperatures and reaction periods for the calcium salt-forming reaction.

TABLE

| Run | % In Solution | (grams) | Titre | Starting Temp. | Low Temp. | High Temp. | Seconds to High Temp. | Seconds to Solid Formation |
|---|---|---|---|---|---|---|---|---|
| | Bicarbonate | Bicarbonate | Bicarbonate | | | | | |
| 1 | 0 | 0 | 0 | 95.0° C. | 75.5° C. | 106.3° C. | 72 | 149 |
| 2 | 2.4 | 0.73 | 5.8 | 92.3 | 76.7 | 105.7 | 87 | 114 |
| 3 | 2.4 | 0.73 | 5.8 | 91.4 | 77.4 | 107.3 | 85 | 120 |
| 4 | 2.4 | 0.73 | 5.8 | 95.0 | 85.2 | 103.8 | 132 | — |
| 5 | 4.2[1] | 1.28 | 10.0 | 91.8 | 75.8 | 103.7 | 215 | — |
| 6 | 10.0 | 3.06 | 26.0 | 91.4 | 73.8 | 100.4 | 352 | 440 |
| 7 | 10.0 | 3.06 | 26.0 | 92.4 | 79.3 | 100.9 | 210 | — |
| | Soda Ash | Soda Ash | Soda Ash | | | | | |
| 8 | 1.5 | 0.46 | 5.8 | 92.2 | 74.5 | 105.0 | 109 | 209 |
| 9 | 2.6 | 0.80 | 20.0 | 86.0 | 68.8 | 101.1 | 456 | — |
| 10 | 5.3 | 1.62 | 20.0 | 90.2 | 72.8 | 101.2 | 255 | 336 |

[1]Residual effluent aqueous medium; Church & Dwight Co., Inc. sodium bicarbonate manufacturing plant, Old Fort, Ohio.

What is claimed is:

1. A process for the preparation of a fatty acid salt product which comprises (1) forming an admixture of reactive ingredients comprising (a) at least one $C_{14}$-$C_{22}$ fatty acid, (b) calcium oxide in at least an equivalent weight quantity for salt formation with the fatty acid, and (c) between about 10–50 weight percent, based on the weight of fatty acid, of an aqueous solution of sodium carbonate-bicarbonate, wherein the aqueous solution is a residual effluent from a sodium bicarbonate-producing process, and the solution contains between about 0.2–5 weight percent of sodium in the form of sodium carbonate-bicarbonate; and (2) recovering the salt product after completion of the exothermic salt-forming reaction.

2. A process in accordance with claim 1 wherein the fatty acid ingredient is a mixture comprising 0–10 percent lauric acid, 0–60 percent palmitic acid, 0–10 percent stearic acid, 0–60 percent oleic acid, and 0–10 percent linoleic acid.

3. A process in accordance with claim 1 wherein the exothermic salt-forming reaction medium is at a temperature between about 60°–110° C.

4. A process in accordance with claim 1 wherein water evaporation occurs during the salt-forming reaction, and the salt product is recovered in the form of friable granules.

* * * * *